US006420583B1

(12) United States Patent
Lienhard et al.

(10) Patent No.: US 6,420,583 B1
(45) Date of Patent: Jul. 16, 2002

(54) METHODS OF SYNTHESIZING RUTHENIUM AND OSMIUM COMPOUNDS

(75) Inventors: Michael Alexander Lienhard, Buffalo; Cynthia A. Hoover, Grand Island, both of NY (US)

(73) Assignee: Praxair Technology, INC, Danbury, CT (US)

( * ) Notice: Subject to any disclaimer, the term of this patent is extended or adjusted under 35 U.S.C. 154(b) by 3 days.

(21) Appl. No.: 09/963,452

(22) Filed: Sep. 27, 2001

(51) Int. Cl.⁷ .................................................. C07F 15/00
(52) U.S. Cl. ........................ 556/136; 556/21; 556/28; 556/137; 427/248.1
(58) Field of Search ........................ 556/21, 28, 136, 556/137; 427/248.1

(56) References Cited

U.S. PATENT DOCUMENTS 6,114,557 A * 9/2000 Uhlenbrock et al. ..... 427/248.1

FOREIGN PATENT DOCUMENTS

WO  WO 00/12766  * 3/2000

OTHER PUBLICATIONS

Leadbeater, Nicholas E., Journal of Organometallic Chemistry, vol. 573, No. 1–2, pp. 211–216 (1999).*

* cited by examiner

*Primary Examiner*—Porfirio Nazario-Gonzalez
(74) *Attorney, Agent, or Firm*—Bernard Lau

(57) ABSTRACT

This invention is directed to a method for synthesizing a carbonyl based compound under neat conditions comprising refluxing a metal carbonyl compound with an excess of neutral ligand to produce a first mixture; evaporating any excess neutral ligand from the first mixture to produce a second mixture; and distilling the second mixture to produce the carbonyl based compound.

8 Claims, No Drawings

METHODS OF SYNTHESIZING RUTHENIUM AND OSMIUM COMPOUNDS

FIELD OF THE INVENTION

This invention is related to a method of synthesizing organometallic materials. More specifically, this invention is directed to a method for synthesizing ruthenium and osmium compounds.

BACKGROUND OF THE INVENTION

Ruthenium (Ru), osmium (Os), and their oxides are materials under consideration for use as electrodes in future semiconductor devices (e.g. ferroelectric memory and logic chips). These materials possess attractive physical properties, such as low electrical resistance, high work functions, inter-layer chemical diffusion resistance, and thermal and oxidative stability. In addition, Ru, Os and their oxides produce thin films with lattice parameters and thermal expansion coefficients that make them compatible with many dielectric materials under consideration for future semiconductor devices.

Chemical vapor deposition (CVD) is a technique that is widely utilized in the fabrication of semiconductor devices to produce the layers of materials that make the devices. CVD chemical compounds (referred to as precursors) are transported in the vapor phase to or near a surface where they decompose by some means (e.g. thermal, chemical or plasma activation) to produce a solid film of a desired material composition. The use of CVD techniques to produce both ruthenium and ruthenium oxide thin films for semiconductor devices has been demonstrated in a number of publications. See, for example, WO 00/12766. Ruthenium and osmium compounds suitable for use as CVD precursors will be required if these materials are incorporated into commercial semiconductor devices using the CVD technique. Further, there have been promising reports of employing both cyclopentadienyl ruthenium (II) complexes and ruthenium (0) carbonyl complexes as CVD precursors. U.S. Pat. No. 6,114,557 discloses a synthetic route to the ruthenium (0) carbonyl complexes.

The preparation of compounds with the formula $L_xM(CO)_Y$ [L=a neutral ligand, M=Ru or Os, x=1 to 4, and y=1 to 5] dates back to the late 1960's when their preparation was first described in the scientific literature. The general preparative route to these compounds involves the reaction of $Ru_3(CO)_{12}$ with a ligand, in the presence of a solvent at reflux. The solvent of choice for these reactions was generally benzene. Reactions of $Ru_3(CO)_{12}$ with dienes, thiols and phosphines occurred in the solvent benzene at reflux. See, Johnson et al., Nature, 1967, pp. 902–3. Preparation of (diene)Ru(CO)$_3$ complexes including $C_6H_8Ru(CO)_3$ and $C_8H_{12}Ru(CO)_3$ complexes were prepared from the reaction of $Ru_3(CO)_{12}$ with 1,3-cyclohexadiene and 1,5-cyclooctadiene respectively, in refluxing benzene. See, Cowles, et al., Chem. Comm, 1969, p. 392.

A second route to [(diene)Ru(CO)$_3$] compounds involves displacement reactions using $C_8H_{12}Ru(CO)_3$ as the starting material. As described above, this compound is prepared by refluxing in benzene a mixture of 1,5-cyclooctadiene and $Ru_3(CO)_{12}$. The $C_8H_{12}Ru(CO)_3$ is then reacted with another diene (for example $C_6H_8$) also in refluxing benzene, to produce the desired product. See, Burt et al., J.C.S. Dalton, 1975, pp. 731–6. Further, alkene ligands displaces $C_8H_{12}$ to form (alkene)Ru(CO)$_3$ complexes, with high yields. See, Domingos, et al., J.C.S. Dalton, 1975, pp. 2288–91.

Finally, U.S. Pat. No. 6,114,557 discloses an improved route to compounds with the formula $L_xM(CO)_Y$ [L=a neutral ligand, M=Ru or Os, x=1 to 4, and y=1 to 5]. The reaction route they utilize is nearly identical to that described above, except that the solvent system is slightly modified. Thus, $Ru_3(CO)_{12}$ is reacted with a ligand, in a solvent other than benzene. Specifically higher boiling solvents (for example toluene) are employed. The '557 patent discloses that a higher boiling solvent system leads to an increased reaction rate and increased product yield.

Although there is a great deal of prior art in the scientific chemical literature disclosing information about compounds of the type $L_xM(CO)_Y$ [L=a neutral ligand, M=Ru or Os, x=1 to 4, and y=1 to 5], it is believed that the synthetic schemes discussed above describes their synthesis.

While prior art solutions employ a non-reactive solvent system for the synthesis of compounds of the type $L_xM(CO)_Y$ [L=a neutral ligand, M=Ru or Os, x=1 to 4, and y=1 to 5], there has been no teaching or suggestion for a neat, or solvent-free, reaction route. In addition, the prior art references show that the synthesis of carbonyl-based complexes, i.e., ruthenium complexes, to require a long reaction time. For example, in U.S. Pat. No. 6,114,557, a reaction which produces $(C_6H_8)Ru(CO)_3$ is reported to take place over a 24 hour time period. Therefore, it is desirous to have a novel neat synthesis approach (where the ligand, L, acts as both the solvent and as a reactant) that is not taught or suggested by the prior art. The neat reaction route enables the reaction to be accomplished more quickly than by using prior art methods, while still producing the desired product in high yield. Using a neat reaction system is also preferable because it simplifies the synthetic process, since fewer components are needed.

SUMMARY OF THE INVENTION

This invention is directed to a method for synthesizing a carbonyl-substituted compound under neat conditions comprising refluxing a metal carbonyl compound with an excess of neutral ligand to produce a first mixture; evaporating any excess neutral ligand from the first mixture to produce a second mixture; and distilling the second mixture to produce the carbonyl based compound. The metal carbonyl is a ruthenium or osmium carbonyl complex. The neutral ligand may be phosphines, phosphites, amines, arsines, stibenes, ethers, sulfides, alkylidenes, nitrites, isonitriles, thiocarbonyls, linear, branched, or cyclic monoalkenes, linear, branched, or cyclic dienes, linear, branched, or cyclic trienes, bicyclic alkenes, bicyclic dienes, bicyclic trienes, tricyclic alkenes, tricyclic dienes, tricyclic trienes, and alkynes.

This invention is also directed to a method for synthesizing a carbonyl-based compound having the formula $L_xM(CO)_y$, wherein L=a neutral ligand, x=1–4, M=Ru or Os and y=1–5, under neat conditions comprising refluxing a metal carbonyl compound with the formula $M_n(CO)_z$, where M=Ru or Os, n=3, z=12, with an excess of neutral ligand to produce a first mixture; evaporating any excess neutral ligand from the first mixture to produce a second mixture; and distillation of the second mixture to produce the carbonyl based compound. The carbonyl is based on the formula $L_xM(CO)_y$, wherein L is a neutral ligand, x=1, M=Ru or Os and y=3.

This invention is also directed to synthesizing a carbonyl-based compound under neat conditions comprising refluxing a metal carbonyl compound with an excess of neutral ligand to produce a first mixture and distilling any excess neutral ligand from the first mixture to produce a second mixture; and distilling the second mixture to produce the carbonyl-based compound.

Furthermore, this invention provides a method for synthesizing a ruthenium complex under neat conditions refluxing a metal carbonyl compound with the formula $M_n(CO)_z$, where M=Ru, n=3, z=12, with an excess of neutral ligand to produce a first mixture; evaporating any excess neutral ligand from the first mixture to produce a second mixture; and distilling the second mixture to produce the carbonyl-based compound. Here, the ruthenium based complex comprises the formula $L_xM(CO)_y$, wherein $L=C_6H_8$, x=1, M=Ru and y=3.

This invention is also directed to a method for synthesizing an osmium complex under neat conditions to reflux a metal carbonyl compound with the formula $M_n(CO)_z$, where M=Os, n=3, z=12, with an excess of neutral ligand to produce a first mixture; vaporating any excess neutral ligand from the first mixture to produce a second mixture; distilling the second mixture to produce the carbonyl based compound. The carbonyl based compound can be described by the formula $L_xM(CO)_y$, wherein $L=C_6H_8$, x=1, M=Os and y=3.

As used herein, the method for synthesis takes the steps of several steps. The word reacting is used, but this term, for purposes of this invention, is interchangable with related terms such as mixing, combining, stirring, refluxing, heating, etc. No reaction necessarily takes place, but a chemical reaction is not precluded. The removing steps can be described as evaporating, distilling, precipitating, filtering, separating, etc.

DETAILED DESCRIPTION OF THE PREFERRED EMBODIMENT

The present invention potentially reduces the volume of material the reaction apparatus must hold to produce similar amounts of product, minimizing the size of the reaction apparatus. Using a similar argument, the absence of solvent also reduces the energy that must be added to the system to bring the mixture to reflux. In addition, after the reaction has been completed, the excess ligand can be more easily recovered/recycled for reuse in this process because it can be distilled directly from the reaction products in high purity, and with a high recovery yield.

To produce compounds of the general type $L_xM(CO)_y$ [L=a neutral ligand, M=Ru or Os, x=1–4, and y=1–5], $M_a(CO)_b$ [where M=Ru or Os], a=1–3, b=5–12, is reacted directly with L under neat conditions (in the absence of a solvent system). Most preferably, the reaction is accelerated by providing a large excess of the ligand L, heating the reaction mixture (ideally to reflux, although other temperatures are allowed and may be desired), and agitating the reaction mixture.

EXAMPLE 1

A preferred embodiment of this invention is described herein.

$Ru_3(CO)_{12}$ (2.0 g, 3.13 mMol) was transferred into an dry 25 mL. round bottom flask equipped with a water-cooled condenser and teflon coated magnetic stirbar. 1,3-cyclohexadiene (5 mL., 52.5 mMol, >5×excess) was added using a syringe. The mixture was heated to reflux with stirring under a dry nitrogen atmosphere for 5 hours, resulting in a clear yellow solution. Heating was stopped and the mixture was allowed to cool to room temperature. Rotary evaporation was employed to remove excess 1,3-cyclohexadiene. Vacuum distillation at 0.1 torr, yielded 1,3-cyclohexadiene ruthenium tricarbonyl, $(C_6H_8)Ru(CO)_3$, (2.1 g, 7.92 mMol, 84% yield) as a pale yellow liquid.

This compound was characterized by using GC-MS, $^1H$ NMR, $^{13}C$ NMR, FTIR, and ICP-MS (metal content).

EXAMPLE 2

Another example in which triosmium dodecacarbonyl, $Os_3CO_{12}$ and 1,3-cyclohexadiene is expected to produce 1,3-cyclohexadiene osmium tricarbonyl, $(C_6H_8)Os(CO)_3$. This reaction is performed under identical conditions as in Example 1 above. 2 g of $Os_3CO_{12}$ (2.2 mMol) is placed into a flask. Then approximately 5 mL. of 1,3-cyclohexadiene (52.5 mMol >5×excess) is added, and the mixture is brought to reflux for several hours. The reaction with osmium in place of ruthenium occurs in similar yield, physical properties, and reactivity. This falls under the generally accepted periodic behavior of the elements.

The most preferable process steps for production of ruthenium and osmium compounds in this invention is as follows:

EXAMPLE 3

87.26 g (0.136 moles) $Ru_3(CO)_{12}$ was placed inside a 3-neck RB flask equipped with a Teflon coated magnetic stir-bar, condenser, and gas cock. 220 mL (185 g, 2.31 moles) of $C_6H_8$ was added. The apparatus was flushed with $N_2$ and subsequently kept under $N_2$ for the remainder of the procedure. The mixture was heated to gentle reflux and stirred for 44 hours, at which point it was a turbid yellow/orange mixture. Atmospheric pressure of this mixture yielded 120 mL. of unreacted $C_6H_8$ at 80 C. Vacuum distillation of the remaining mixture (at P=0.1 torr) yielded 103.32 grams of $(C_6H_8)Ru(CO)_3$ (0.39 moles, 95% yield) at (>99.8% by GC-MS).

The excess ligand is removed by distillation. The refluxed reaction mixture was rotary-evaporated at ≈10 Torr and 60° C., which removes the excess 1,3-$C_6H_8$ due to its lower relative vapor pressure to remove the non-reactive solvent and the excess ligand. Finally, the resulting refluxed reaction mixture in which the ligand was removed is distilled at ≈$10^{-2}$ Torr, yielding $C_6H_8Ru(CO)_3$ at a head temperature of 40° C.

This invention may be practiced using other carbonyl compounds. Although $M_3(CO)_{12}$ [M=Ru or Os] are know to be the most thermodynamically stable compound consisting entirely of the metal and carbonyl (CO) groups, other metal carbonyl compounds could be employed.

A number of other ligands of potential use are possible other than cyclic dienes. These include any neutral or neutral pi-donating ligand. For example, linear, cyclic or branching alkenes, dienes, trienes, etc., sulfides, ethers, amines, phosphines, and nitriles may be successfully employed. These general classes of compounds include hydrogen, fluorine, other halogen or other organic substitutents.

Relative to the reactant stiochiometry, the proportion (in number of molecules) of the ligand to the starting metal carbonyl effects the rate of reaction. The solubility of the metal carbonyl, intermediates and reaction products in the ligand, and availability of the ligand to react (sterically, energetically, and kinetically) all effect the reaction rate and yield.

The temperature of reaction affects the reaction rate. In general, an increase in temperature leads to an increase in reaction rate, generally following Arrhenius behavior. In addition the temperature of the ligand is expected to effect the solubility of the metal carbonyl starting materials or intermediates in the reaction mixture. In this invention, the temperature is kept moderated so as not to cause thermal decomposition of the starting materials, intermediates, or final products in a way deleterious to the desired reaction.

Sufficient mixing of the reactants increases the reaction rate and decreases the time of reaction. Agitation may be performed by any physical means (stirring, shaking, sonication etc.).

The reaction pressure influences the rate of reaction and yield of products. The pressure of reaction will effect the partial pressures, and boiling points (temperatures) of the reactants. Tailoring the pressure/temperature of the system is to optimize reaction time, yield and purity.

Thus, all of these variables would be expected to have influence on the time required to complete the reaction, product yield, and product purity.

This invention may use starting materials such as any ruthenium or osmium carbonyl complex, preferably $M_a(CO)_b$, where a=1–3 and b=5–12, and most preferably $M_3(CO)_{12}$.

The ligand may be any neutral coordinating ligand, and any mixture possible thereof, preferably monoalkenes, dienes, trienes (linear, branched or cyclic), phosphines ($R_3P$), amines ($R_3N$), ethers ($OR_2$), sulfides ($SR_2$). The R group, generally hydrocarbon group, may contain hydrogen, fluorine or any organic group. Most preferably, the ligand is a pure, linear, branched or cyclic diene (e.g. 1,3-cyclohexadiene).

The stoichiometric ratio of ligand to metal may be any amount, preferably any excess of ligand to metal carbonyl, and most preferably a substantial excess of ligand to metal carbonyl.

The reaction temperature may be any temperature above the freezing point of the solvent to any temperature below the decomposition temperature of the starting material, ligands, reactive intermediates, or products, preferably any temperature above ambient, and most preferably at atmospheric boiling temperature of L (provided that at this temperature there is minimal thermal decomposition of the starting material, ligands, reactive intermediates, or products).

The reaction pressure may be sub-atmospheric to high pressure. Preferably, the pressure of the reaction is above or below atmospheric pressure, and tailored to allow reflux of the reaction mixture at desired reaction temperature, and most preferably at atmospheric pressure.

The reaction may take place at any atmosphere. Preferably, the reaction takes place in the presence of an atmophere containing xenon, neon, helium, carbon monoxide and carbon dioxide. More preferably, the reaction takes place in the presence of an inert gas such as argon or nitrogen.

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed is:

1. A method for synthesizing a carbonyl-based compound having the formula $L_xM(CO)_y$, wherein L=a neutral ligand, x=1–4, M=Ru or Os and y=1–5, under neat conditions comprising
    a. reacting a metal carbonyl compound with the formula $M_a(CO)_b$, where M=Ru or Os, a=1–3, b=5–12, with an excess of neutral ligand to produce a first mixture;
    b. removing any excess neutral ligand from said first mixture to produce a second mixture;
    c. distilling said second mixture to produce said carbonyl based compound.

2. The method of claim 1 wherein said carbonyl based compound comprises the formula $L_xM(CO)_y$, wherein $L=C_6H_8$, x=1, M=Ru and y=3.

3. The method of claim 1 wherein said carbonyl based compound comprises the formula $L_xM(CO)_y$, wherein $L=C_6H_8$, x=1, M=Os and y=3.

4. The method of claim 1 wherein said neutral ligand is a ligand selected from the group consisting of phosphines, phosphites, amines, arsines, stibenes, ethers, sulfides, alkylidenes, nitrites, isonitriles, thiocarbonyls, linear, branched, or cyclic monoalkenes, linear, branched, or cyclic dienes, linear, branched, or cyclic trienes, bicyclic alkenes, bicyclic dienes, bicyclic trienes, tricyclic alkenes, tricyclic dienes, tricyclic trienes, and alkynes.

5. A method for synthesizing a ruthenium complex under neat conditions
    a. reacting a metal carbonyl compound with the formula $M_n(CO)_z$, where M=Ru, n=3, z=12, with an excess of neutral ligand to produce a first mixture;
    b. removing any excess neutral ligand from said first mixture to produce a second mixture;
    c. distilling said second mixture to produce said carbonyl-based compound.

6. The method of claim 5 wherein said ruthenium based compound comprises the formula $L_xM(CO)_y$, wherein $L=C_6H_8$, x=1, M=Ru and y=3.

7. A method for synthesizing an osmium complex under neat conditions
    a. reacting a metal carbonyl compound with the formula $M_n(CO)_z$, where M=Ru, n=3, z=12, with an excess of neutral ligand to produce a first mixture;
    b. removing any excess neutral ligand from said first mixture to produce a second mixture;
    c. distilling said second mixture to produce said carbonyl based compound.

8. The method of claim 7 wherein said osmium based compound comprises the formula $L_xM(CO)_y$, wherein $L=C_6H_8$, x=1, M=Os and y=3.

* * * * *